United States Patent [19]
Golding et al.

[11] Patent Number: 5,324,177
[45] Date of Patent: Jun. 28, 1994

[54] SEALLESS ROTODYNAMIC PUMP WITH RADIALLY OFFSET ROTOR

[75] Inventors: Leonard A. R. Golding, Moreland Hills; William A. Smith, Lyndhurst, both of Ohio

[73] Assignee: The Cleveland Clinic Foundation, Cleveland, Ohio

[21] Appl. No.: 695,312

[22] Filed: May 3, 1991

Related U.S. Application Data

[63] Continuation-in-part of Ser. No. 349,000, May 8, 1989, Pat. No. 5,049,134.

[51] Int. Cl.⁵ .................................... F04B 17/00
[52] U.S. Cl. ........................ 417/423.1; 417/423.7; 604/151; 415/900
[58] Field of Search ............ 417/423.1, 423.7, 354; 604/151; 415/900

[56] References Cited

U.S. PATENT DOCUMENTS

| | | | |
|---|---|---|---|
| 3,420,184 | 1/1969 | Englesberg et al. | 623/3 |
| 3,608,088 | 9/1971 | Dorman et al. | 633/3 |
| 3,647,324 | 3/1972 | Rafferty et al. | 623/3 |
| 3,960,468 | 6/1976 | Boorse et al. | 417/423.13 |
| 4,135,253 | 1/1979 | Reich et al. | 415/900 |
| 4,382,199 | 5/1983 | Isaacson | 417/423.12 |
| 4,625,712 | 12/1986 | Wampler | 415/900 |
| 4,645,733 | 2/1987 | Hauenstein | 417/420 |
| 4,688,998 | 8/1987 | Olsen et al. | 415/900 |
| 4,704,121 | 11/1987 | Moise | 623/3 |
| 4,714,405 | 12/1987 | Schaefer et al. | 417/366 |
| 4,806,080 | 2/1989 | Mizobuchi et al. | 417/353 |
| 4,812,108 | 3/1989 | Kotera | 417/423.13 |
| 5,049,134 | 9/1991 | Golding et al. | 604/151 |

*Primary Examiner*—Richard A. Bertsch
*Assistant Examiner*—Alfred Basichas
*Attorney, Agent, or Firm*—Fay, Sharpe, Beall, Fagan, Minnich & McKee

[57] ABSTRACT

A sealless centrifugal blood pump is provided in which a rotatable impeller is supported in a pump housing by fluid bearings during operation. Rotational movement of the impeller is accomplished with an inverted motor for magnetically driving of the impeller and maintenance of the axial running position of the impeller relative to the housing. In an alternative embodiment, the axis of the rotor housing is radially displaced relative to the axes of drive element of the motor and the motor housing.

41 Claims, 6 Drawing Sheets

SEALLESS ROTODYNAMIC PUMP WITH RADIALLY OFFSET ROTOR

BACKGROUND OF THE INVENTION

This application is a continuation-in-part application of pending U.S. Ser. No. 349,000, filed May 8, 1989, now U.S. Pat. No. 5,049,134.

This invention pertains to the art of pumps and more particularly to electrically driven pumps capable for use as heart or blood pumps, or ventricular assist devices.

The invention is applicable to a pump for the pumping of blood of a living person, or animal, to replace or assist the pumping function of the biologic heart. It is capable of being sized and designed to fit inside a pumping chamber of a human heart, e.g. dimensioned on the order of a few inches. However, certain aspects of the invention could be readily configured for use in other environments than a blood pump wherein the presence of a shaft seal or long fluid residence times in the pump would be detrimental to the application.

In the preferred environment, conventional continuous flow rotodynamic blood pumps, which includes centrifugal blood pumps, axial flow blood pumps, or nonpulsatile blood pumps, have suffered from a number of problems. One major difficulty has been the presence of a shaft seal. Loss of blood from the circulatory system, and/or introduction of material of damaging types or quantities into the circulatory system must be prevented. Because of the intended use as life support for a human being, long life and utter reliability are key design goals. Using a contact type seal or fluid purged seal as the shaft seal results in significant difficulties meeting these objectives.

Most commercially available blood pumps, as exemplified by U.S. Pat. Nos. 4,135,253 to Reich, et al., 4,625,712 to Wampler, 3,647,324 to Rafferty, et al., or 4,589,822 to Clausen et al., have a blood pumping impeller mounted on a shaft which penetrates a side wall of the pumping cavity by means of a shaft seal. On the non-blood side of the seal, or drive compartment, is a motor or drive magnet, operating in air or a biocompatible fluid, which rotates the impeller via the shaft. A very common cause of failure of such prior known blood pumps is the eventual leakage of the seal about the shaft which either permits blood to enter into the drive compartment, excessive fluid leakage from the non-blood side into the blood, or both.

Other blood pump structures have been proposed to overcome the problems of blood pump shaft seals. Moise has a non-contacting housing-shaft interface with micron sized clearances that unfortunately introduce significant problems. Attempting to maintain these close dimensional tolerances clearly becomes a manufacturing problem. Additionally, there is a risk of blood leakage if the supply of purge fluid to the non-blood seal of the pump is interrupted.

Dorman U.S. Pat. No. 4,927,407 suggests using a constant flow pump such as a dynamic perfusion pump to supply a continuous, controlled flow of purge fluid to the seal. The purge fluid flow maintains the seal out of contact with the shaft. Unfortunately, this adds significant complication to the system because of the need for another active control pump and, even then, still requires a purge fluid for normal operation.

Alternatively, it has been suggested to magnetically suspend the impeller in three dimensions. This eliminates the need to breach the pump walls with a shaft to the impeller. Bramm, et al. and Moise generally illustrate this approach. However, at best this is a complex system because of its three dimensional nature, and is not presently believed to be commercially feasible.

Still other blood pumps have eliminated a penetrating shaft and accompanying seal by magnetically coupling the pump to a prime mover through a wall of the housing. Dorman U.S. Pat. No. 3,608,088 is an example of one such arrangement from the blood pump field. Although these eliminate leakage, they may amplify other problems also present in shaft sealed designs.

For example, high shear stresses around the seal, or around radial and axial bearings, can damage blood if the loads and shear stresses are not very low. Axial magnetic coupling, such as exemplified by Dorman, particularly creates an axial load which must be reacted or countered. Both shear and mechanical friction forces can produce heat that injures susceptible media. With blood, heat produced from the shear and friction forces can also promote deposition, including protein buildup, as well as a conventional clot.

Residence time is also a factor in handling some fluids such as blood. The amount of shear that blood can tolerate is a function of exposure time. Blood coagulation, leading to clots and emboli, also requires a finite time to occur. Thus many pump structures and principles derived from pumps in other fields are not suitable in the blood pump environment since they include relatively stagnant areas where the blood can settle out, react, decompose, or otherwise respond according to the environment and their sensitivity.

Some alternate pump design proposals employ a counter-impeller to prevent backflow along the shaft. This is particularly well known in other pump environments, i.e., non-blood pumps where the dynamic action of a counter-impeller provides a back flow along the shaft. These arrangements hold pumped fluid for long periods in the expeller, thus exposing the pumped fluid to shear. Therefore, these structures are not feasible for use as blood pumps because of all the problems described above associated with long residence times and shear. Further, these arrangements could accelerate leakage into the system if the second impeller discharges its prime of pumped fluid. Even further, these pump arrangements still require additional sealing in order to prevent fluid loss at static or low speed conditions.

The present invention contemplates a new and improved device which overcomes all of the above discussed problems and others to provide a new blood pump.

BRIEF SUMMARY OF THE INVENTION

According to the present invention, there is provided a new rotodynamic blood pump which is capable of being implanted in a human body to assist or replace the pumping functions of the heart. The pump includes a rotor rotatably received in a pump chamber. The rotor is suspended in the chamber by fluid bearing means, preferably provided by an axial extension of the housing. Means for renewing fluid contact with all wetted surfaces of the chamber is also provided.

According to a more limited aspect of the invention, the pump comprises a housing having inlet and outlet fluid passages communicating with a pump chamber. An end wall extends axially into the chamber and defines a journal surface to support radial loads. An annular rotating assembly, or shaftless rotor, is received in the pump chamber and is driven by a drive means having a drive element and a driven element for selective rotation relative to the housing. The rotor includes both pumping blades and the driven element of the drive means. The annular rotor cooperates with the axial extension to define two fluid passages. The primary fluid passage leads from the inlet to the outlet, while the second passage permits a continuous flow to be delivered to otherwise potentially stagnant areas of the pump. Further, at least a portion of this second passage is narrowed to form a radial fluid bearing.

According to another aspect of the invention, the rotor is radially magnetically coupled to the drive element of the drive means. The drive means has a central cylindrical element and a surrounding annular element, either one of which is the drive element of the system. Further, the axial running position of the rotor is substantially maintained by the reaction of the drive means magnetic forces to the applied pressure forces on the rotor. Means for limiting the motion of the rotor is also provided.

According to yet another aspect of the invention, a predetermined radial offset is provided between the axes of the rotor and the drive element. This results in a magnetic imbalance force of known magnitude and direction.

According to a still further aspect of the invention, the fluid bearing means includes a groove to increase fluid flow through the bearing means.

According to still another aspect of the present invention, the rotor includes first and second sets of blades. The first blade set has substantially more pumping capacity than the second blade set and defines an impeller or main stage primarily urging the fluid from the inlet to the outlet. The second blade set controls and assists fluid flow through the second passage. Additionally, the second blade set produces a pressure distribution which counteracts that produced by the first blade set, reducing the net force to be reacted in the magnetic coupling.

According to another, yet more limited aspect of the present invention, the rotor includes openings between the primary and secondary flow passages permitting fluid exchange therebetween.

One benefit obtained from the present invention is a sealless pump having a single moving part and improved durability.

Another benefit is the provision of a pump that eliminates flow stasis areas, and maintains surface washing throughout the pump.

A further benefit of the invention is eliminating significant mechanical axial thrust contacts.

Yet another benefit of the invention is a means to stabilize the position and operation of a fluid bearing.

Still other benefits and advantages of the subject invention will become apparent to those skilled in the art upon a reading and understanding of the specification.

BRIEF DESCRIPTION OF THE DRAWINGS

The invention may take physical form in certain parts and arrangements of parts, preferred embodiments of which will be described in detail in this specification and illustrated in the accompanying drawings which form a part hereof and wherein:

FIG. 6 is a schematic illustration of the electromagnetic reaction between a stator and operating rotor in the present invention and is intended to demonstrate the preservation of the desired axial running position of the impeller relative to the housing;

DETAILED DESCRIPTION OF THE PREFERRED EMBODIMENTS

Figure 1:
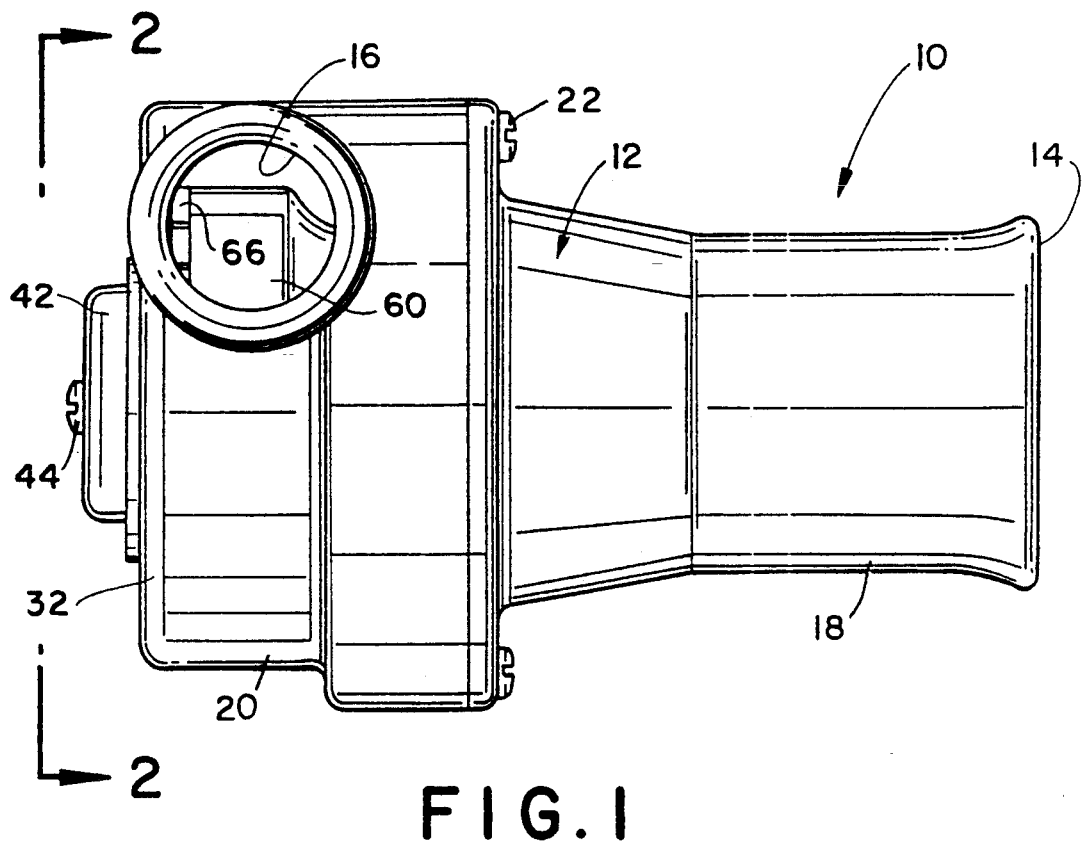
FIG. 1 is a side elevational view of a blood pump formed in accordance with the present invention and particularly showing the pump housing and inlet and outlet passageways.

Referring now to the drawings wherein the showings are for purposes of illustrating the preferred embodiments of the invention only and not for purposes of limiting same, the FIGURES show a pump 10 comprised of a housing 12, and having an inlet 14 and an outlet 16. While the drawings show an axial inlet, and a radial or tangential outlet, these are not essential features of the invention. In the blood application, the pump can be sized for implantation within a living body, and is preferably employed as an assist device for humans. It is to be noted that the pump can be sized so as to even be implantable within a heart chamber, avoiding the substantial problems of larger devices.

Figure 2:
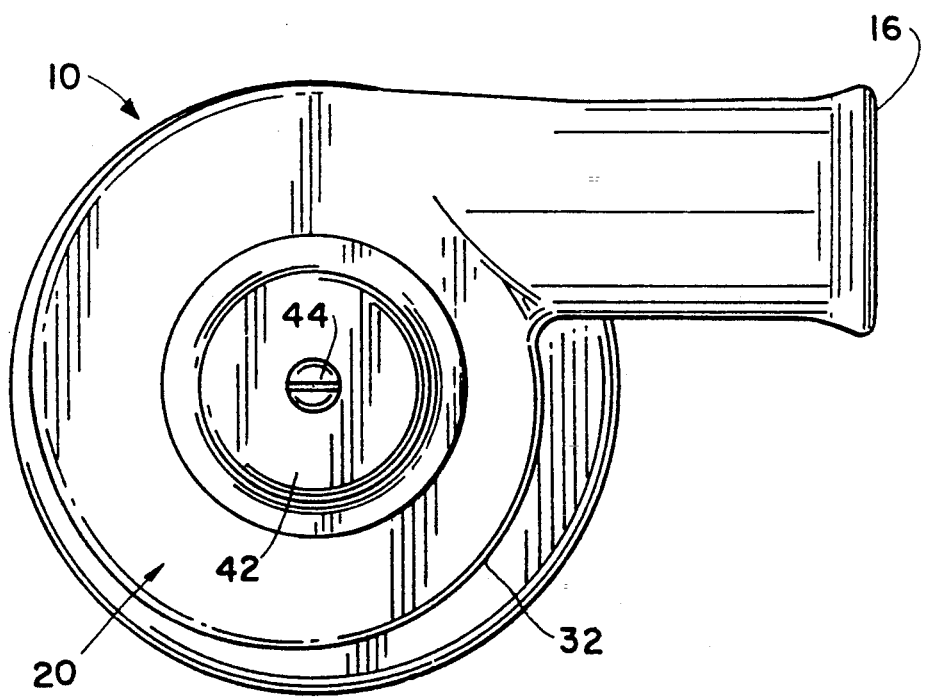
FIG. 2 is a left-hand end view taken generally along the lines 2—2 of FIG. 1.
Figure 3:
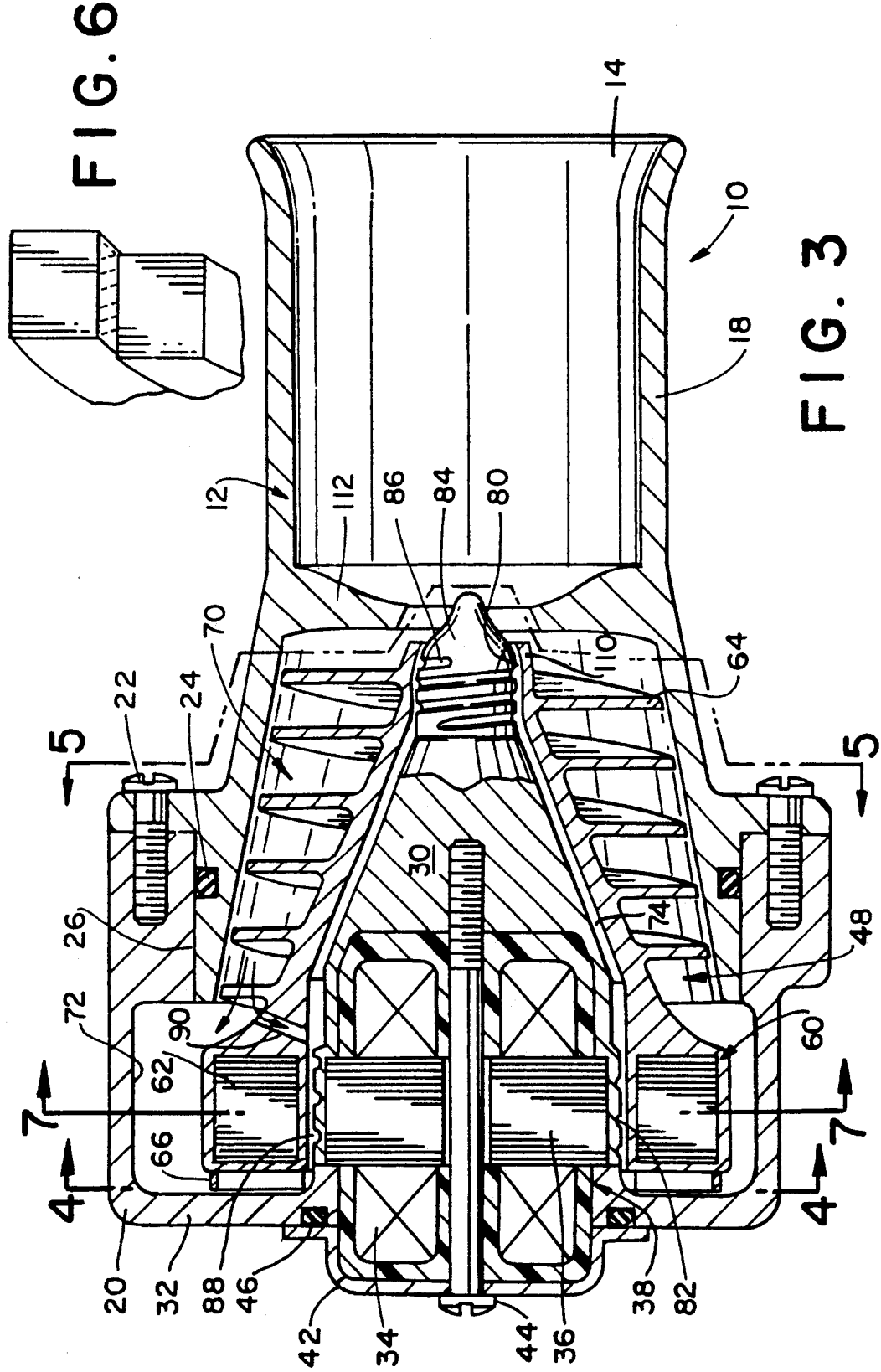
FIG. 3 is an enlarged, longitudinal cross-sectional view of a first preferred embodiment of the subject invention.

With particular reference to FIGS. 1-3, the housing 12 is shown to be more particularly comprised of a rotor portion 18 and a drive housing or outlet portion 20, which in this particular embodiment partially houses the rotor as well as the drive means. Since in the preferred embodiments the pump is adapted for implantation in the living body, the housing portions are formed from a suitable, biocompatible material such as polished titanium. The housing portions 18, 20 are fastened together with conventional fastening devices 22 and sealed with a conventional sealing device such as an O-ring 24. The O-ring is positioned in an area of overlapping engagement 26 which has been made an interference fit or bonded so as to be gap free.

The housing portion 20 incorporates an axial extension 30 protruding from end wall 32. The axial extension receives motor windings 34 and lamination assembly or ferrous stack 36 of an electric motor 38. The motor is retained in the outlet housing portion by cover 42 and a fastener such as screw 44. The cover is sealed to the outlet housing portion with 0-ring 46. The extension 30 protrudes a substantial dimension from the end wall, in fact, extending into the rotor housing portion and toward the inlet 14 This arrangement provides a generally annular pump chamber 48.

Received over the housing extension 30 is an annular rotor 60. The rotor includes an encapsulated permanent magnetic assembly 62, and first and second impeller blade sets 64, 66. There is no interconnecting shaft between the motor and impeller, i.e. a shaftless rotor. Further, a shaft seal between the motor and the impeller is eliminated, thus obviating many of the problems discussed above in prior art structures. In the preferred embodiment, the permanent magnet assembly 62 in the pump rotor 60 radially couples the rotor to the motor stator (stack and windings) through the non-magnetic wall of housing extension 30. It should be noted that this arrangement is essentially an inversion of the usual commercial motor arrangement, because the rotating element of the motor, i.e., the permanent magnetic assembly 62, is larger in diameter and encircles the stationary element, i.e., the stator 34, 36. This electric motor serves as the means for driving this embodiment of the invention insofar as it serves to create rotational motion of the pump rotor relative to the housing. The stator assembly is the drive element and the permanent magnet assembly the driven element of this version of a drive means.

Figure 4:
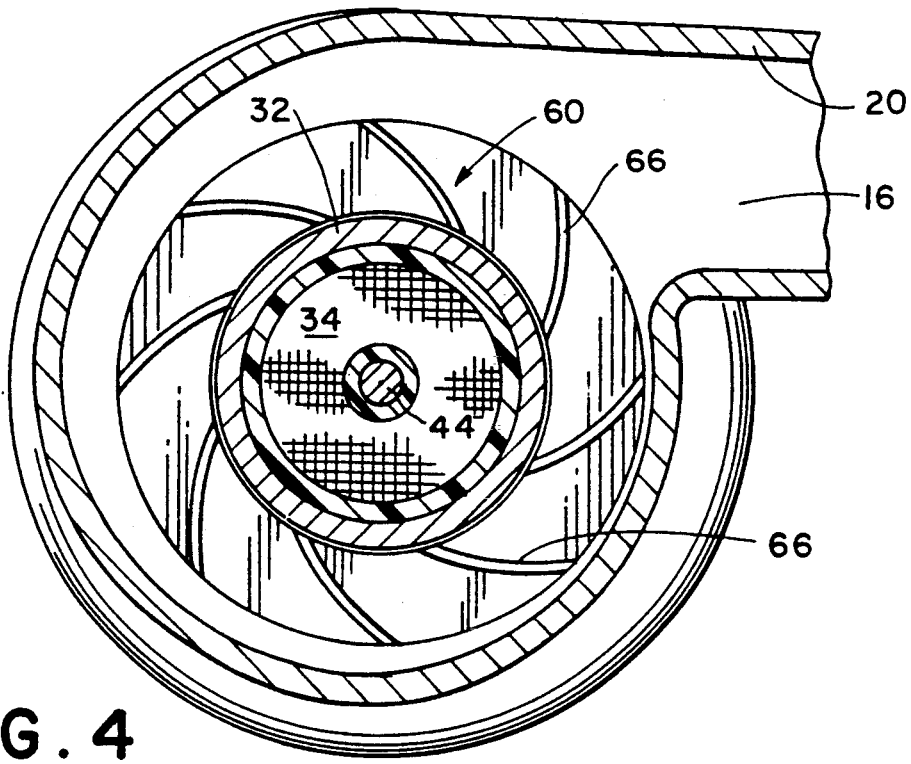
FIG. 4 is a cross-sectional view taken generally along lines 4—4 of FIG. 3.
Figure 5:
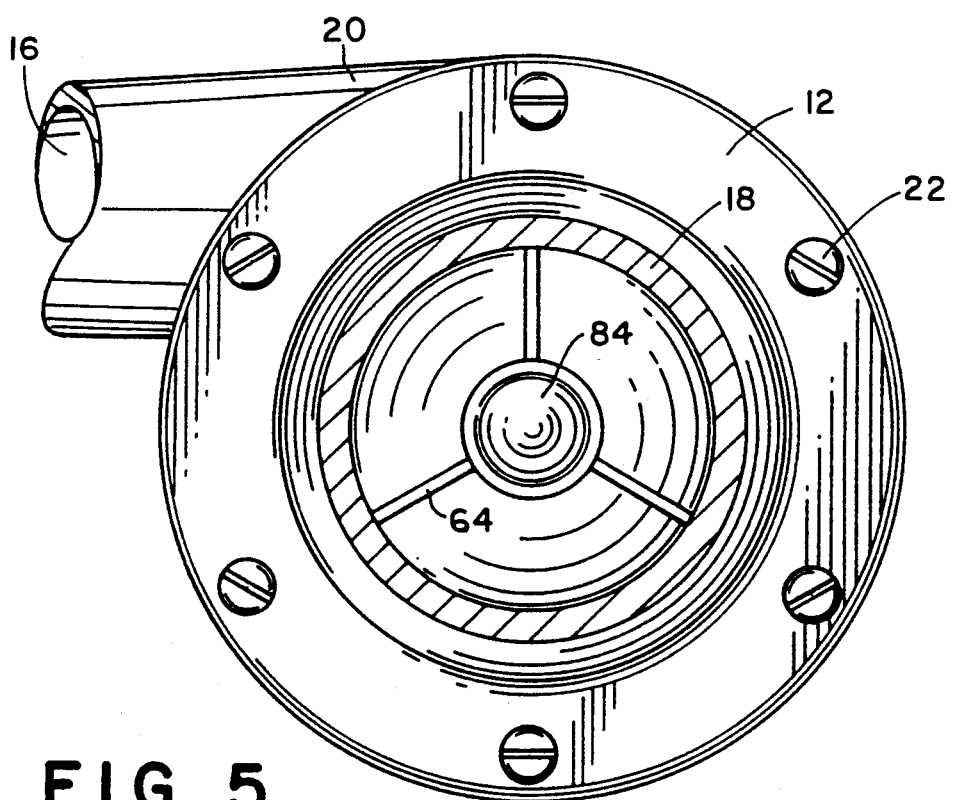
FIG. 5 is a cross-sectional view taken generally along lines 5—5 of FIG. 3.

With particular reference to FIGS. 3 and 4, the first or primary impeller blade set 64 includes a plurality of mixed flow impeller blades. Radial flow or axial flow blade arrangements could also be encompassed within the scope of the invention. The impeller shown is a three-bladed variable lead screw. The secondary impeller blade set 66 is comprised of a plurality of radial flow impeller blades in this design embodiment.

The placement of rotor 60 in the housing 12 defines a continuous, first fluid passage 70 between the rotor 60 and the interior wall of the housing, which traverses from the inlet 14 to the annular output collector 72 of the pump chamber. A continuous second passage fluid passage 74 is formed between the housing extension 30 and the inside diameter of pump rotor 60. The second 74 has a generally large clearance, perhaps 0.020–0.030 inch, compared to the flow to be passed, but narrows to approximately 0.003–0.005 inch at opposite ends of the rotor to define first and second fluid bearings 80, 82 during operation of the pump. The first bearing 80 is located at the terminal end 84 of the portion of the motor housing extension 30 facing the inlet 14. This terminal end portion 84 has a generally cone-like configuration and includes one or more extended helical grooves 86 to increase the lubricating and cooling flow through the fluid bearing 80. The second fluid bearing 82 similarly has a helically configured grooving 88 on the outer wall of the motor housing extension 30 to increase the bearing wash flow.

For improved pumping that avoids fluid damage or deposition due to sluggish or non-existing flow velocities through second passage 74, a continuous washing flow is required. The second set of impeller blades 66 scavenges blood from the second passage, discharging it to the collector 72. To prevent excessive pressure drop, a plurality of circumferentially spaced openings 90 extend generally radially between the first and second fluid passages to permit fluid to flow from the first to the second passage. Under the action of the pressure rise produced by the first blade set 64, flow traverses from openings 90 to impeller inlet 14, along passage 74. The second blade set also draws fluid from openings 90, through bearing 82, past end wall 32 and discharges the fluid into the collector 72.

With particular reference to FIG. 4, it may be seen that the annular collector chamber 72 can be spirally offset relative to the generally circular dimension of the rotor 60. Such a configuration is generally conventional for the volume of a rotodynamic pump, but the present invention may also be used with other forms of discharge collector.

Because the annular pump rotor 60 is freely received in the housing 12, it is important that its motion be controlled so that damage to the pumped fluid or the mechanical components does not result in close clearance areas, such as bearings 80, 82, or at interior walls of the housing. The symmetrical design of the pump permits the radial load to be low, which results in a significant fluid film thickness on the order of 0.001 inch at bearings 80, 82. This avoids mechanical wear on the pump components, and minimizes fluid shear of the blood, both of which are obviously detrimental to the intended use of the pump. On the other hand, if the load is too low, the bearings can go into a well-known whirl mode, destroying the film thickness and the bearings. In this operating mode, instead of rotating around a fixed axis, the rotor rolls 360 degrees around the stator, wearing all surfaces of the rotor and stator.

Figure 7:
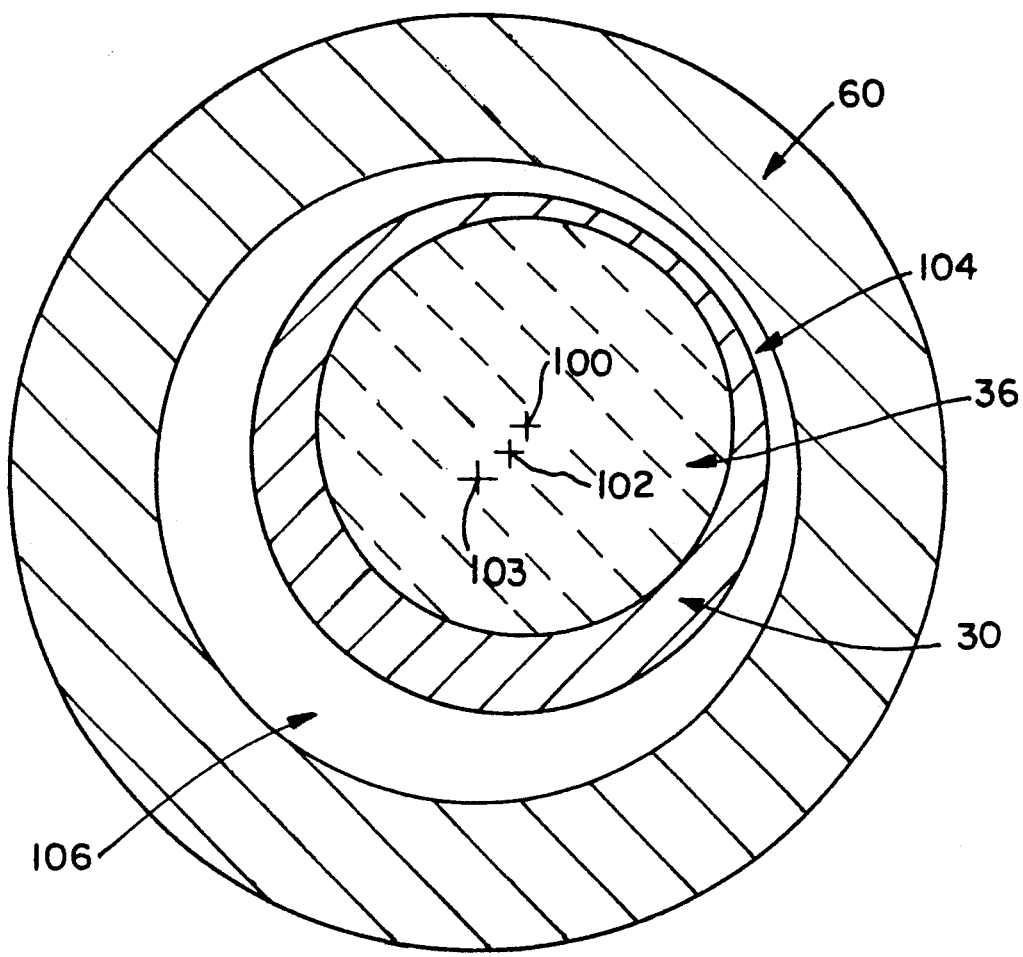
FIG. 7 is a schematic cross-sectional view taken along line 7—7 of FIG. 3 particularly illustrating the predetermined radial offset of pump components.

The subject invention overcomes this problem by purposely and deliberately radially offsetting the centerline 100 of the motor stator relative to the centerline 102 of the drive housing portion 20 (FIG. 7). As a result of this offset, magnetic forces are higher at region 104, and lower at region 106, resulting in a known, controlled magnitude and direction of bearing loading. For example, preliminary tests of pump prototypes in accordance with the subject invention provide an offset on the order of 0.001–0.002 inch which results in magnetic forces of a few tenths of a pound at 104 and at 106. Because of this known force magnitude and direction, it is possible to calculate the running position of the rotor 60 (as represented by numeral 103, which is also representative of the centerline of the drive housing portion 20) and establish another centerline shift between the drive housing portion 20 and the rotor housing portion 18, such that the clearance between the impeller blades 64 and the housing wall is held more uniform around the circumference.

The axial motion of the pump rotor 60 must also be controlled to maintain a desired position of the rotor. The summation of pressure forces acting along the first and second fluid passages 70, 74, respectively, will tend to move the rotor relative to end wall 32. The magnetic attraction forces between the stator 34 and magnet assembly 38 are designed to be sufficient to overcome this tendency, even with slight variation of movement. FIG. 6 illustrates this operation. Axial motion is further limited during transients by the interaction of conical extension 110 on the rotor 60 with the housing cone 84 and inlet stop means which resemble stator blades 112. Should motions occur outside of normal limits, the rotor will contact stop means at controlled points of small diameter and consequent low rubbing velocity. Alternatively, stop means 112 could be replaced by reconfiguring the interior wall at a slightly different angle than that on rotor 60, such that any contact would be in a local, small diameter area adjacent to inlet 14.

Figure 8:
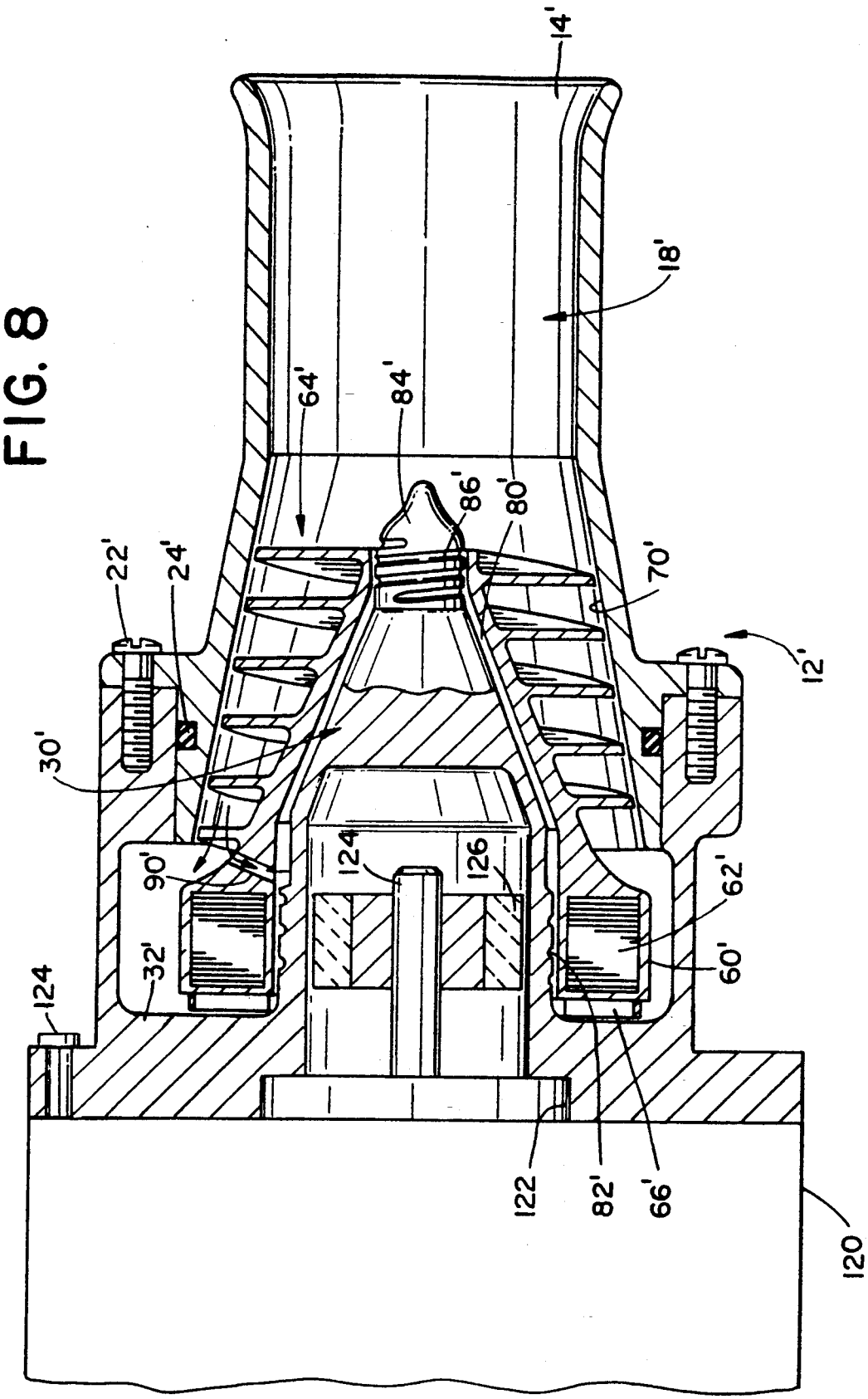
FIG. 8 is a longitudinal cross-sectional view of an alternate embodiment of the invention.

FIG. 8 contains an alternative blood pump in accordance with the teachings of the subject invention. Like elements are referred to by like numerals with a primed (') suffix, while new elements are referenced by new numerals. Pump housing 12' is guidedly mounted to an external prime mover 120 by pilot diameter 122 and quick connect fasteners 124. The prime mover Could be an electric motor, or other suitable means of converting energy to rotary motion of the shaft 124. Fixedly mounted to the shaft 124 of the prime mover is a driver magnet assembly 126. This forms a magnetic coupling with driven magnet assembly 62' as will be understood by those skilled in the art. The driver and driven magnets rotate synchronously under the urging of the motor 120. The motor and magnet assembly functionally replace the stator 34 and coils 36 previously discussed as fixedly mounted in the housing 20 and together constitute the drive element of the drive means of this embodiment of the invention. As other details of construction of this embodiment are substantially identical to those already described except for the omission of the conical extension 110 and stop means 112, they will not be repeated here.

Figure 9:
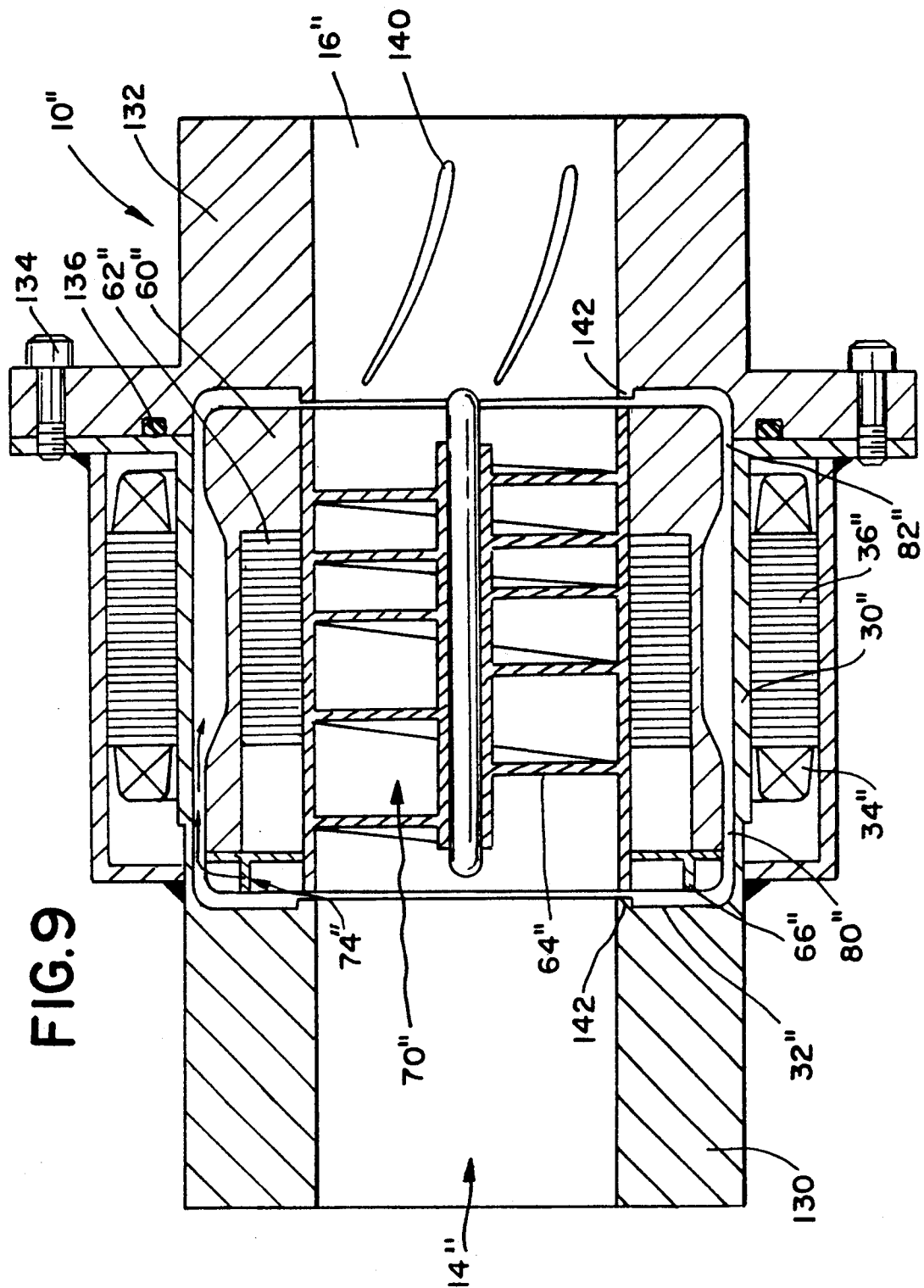
FIG. 9 is another embodiment of the invention showing an alternate version of the drive means.

FIG. 9 illustrates an inverted embodiment of the invention, apparently different in configuration but generally working according to the same principles described above. Like numerals with a double primed suffix (") are used to identify like elements while new numerals refer to new elements.

The pump has a housing 10" having an inlet 14" and an outlet 16". The housing particularly comprises a drive housing portion 130 and a discharge housing portion 132. The housings are retained together by conventional fasteners 134 and sealed by O-rings 136. Installed Within the housing portion 130 is a motor stator 36" and associated Windings 34". Received in the housing portion is pump rotor 60", which comprises permanent magnet assembly 62", and impeller blade sets 64", 66". The primary blade set 64", though, is of axial flow geometry. It is further noted that the motor is now of conventional arrangement with the stator being of larger diameter and surrounding the magnet assembly 62". Axial extension 30" of the end wall 32" of housing forms radial bearing means 80", 83" to support the rotor.

As received in the housing 10", the pump rotor defines primary and secondary flow paths 70", 74", respectively. The primary impeller blades 64" are located in the first flow passage, and urge blood from inlet 14" to outlet 16". Stator blades 140 in the outlet housing slow the blood from and convert velocity into pressure energy. Secondary pump blades 66" urge blood from the inlet through passage 74" to the outlet. In a variation of this design, the secondary blades could be deleted and the wall separating the primary and secondary flow passages eliminated. In this case the primary impeller blades would urge flow through both the primary and "secondary" passage, and the bearing surfaces would be formed by the blade tips. Passage 74" is narrowed at each end of the pump rotor to form first and second fluid bearings 80", 82". As in the previous discussion of FIG. 7, centerline shift can be used to provide a stable load for these bearings. The net force resulting from the summation of pressures acting on the pump rotor is primarily reacted by the magnetic attraction of the stator and magnet assembly as diagrammed in FIG. 6. Transient axial motions, in turn, Can be limited by a plurality of struts 142 on the housing.

The invention has been described with reference to the preferred embodiments. Obviously, modification and alternations will occur to others upon the reading and understanding of the specification. It is our intention to include all such modifications and alterations insofar as they come within the scope of the appended claims or the equivalents thereof.

Having thus described the invention, we now claim:

1. A rotodynamic pump comprising:

a housing having an axis and an inlet and outlet in fluid communication with a chamber;

a rotor having an impeller received in the chamber;

drive means for rotating the rotor relative to the housing including a drive element and a driven element operatively associated with the rotor, the driven element being radially offset/displaced relative to the axis of the drive housing to produce a predetermined radial force of known magnitude and direction;

fluid bearing means for supporting the rotor in the chamber provided by an extension of an end wall of the chamber; and means for continually renewing the fluid in contact with all wetted surfaces of the chamber.

2. The pump as defined in claim 1 further comprising first and second generally radially spaced circumferentially continuous fluid flow passages defined between the housing and the rotor.

3. The pump as defined in claim 2 further comprising means for urging fluid flow through the second passage.

4. The pump as defined in claim 2 further comprising first and second blade sets operatively associated with the rotor, the first blade set pumping fluid from the inlet to the outlet, and the second blade set urging fluid through the second passage.

5. The pump as defined in claim 2 further comprising an opening in the rotor connecting the first and second passages for permitting fluid flow therebetween.

6. The pump as defined in claim 2 wherein the second passage has a narrowed portion to define a fluid bearing of the fluid bearing means.

7. The pump as defined in claim 6 further comprising a groove on a sidewall of the second passage for passing flow through the fluid bearing.

8. The pump as defined in claim 6 wherein the second passage has a second narrowed portion to define a second fluid bearing of the fluid bearing means.

9. The pump as defined in claim 8 further comprising a groove on a sidewall of the second passage for passing flow through the second fluid bearing.

10. The pump as defined in claim 1 further comprising a set of blades on the rotor for urging fluid flow through the fluid bearing means.

11. The pump as defined in claim 10 further comprising thrust reaction means operatively associated with the drive and driven elements for resisting longitudinal displacements caused by axial fluid, gravitational, inertial or other forces.

12. The pump as defined in claim 1 further comprising means for limiting axial travel of the rotor relative to the housing.

13. The pump as defined in claim 1 wherein the longitudinal axis of the rotor housing is offset relative to the longitudinal axes of the drive element and the drive housing to more closely align the rotor housing axis with the rotor axis of rotation during operation.

14. The pump as defined in claim 1 wherein the drive means comprises an electric motor having a rotor portion and a stator portion.

15. The pump as defined in claim 1 wherein the drive means comprises an electric motor with a stator portion smaller in diameter than a rotor portion.

16. The pump as defined in claim 1 wherein the drive means comprises a magnetic coupling in combination with a prime mover.

17. The pump as defined in claim 1 further comprising blood as the fluid.

18. A rotodynamic pump comprising:
a housing having an axis and an inlet and an outlet in fluid communication with a chamber;
a shaftless rotor received in the chamber for selective rotation relative to the housing;
drive means for rotating the rotor relative to the housing including a drive element having an axis and a driven element operatively associated with the rotor, the axis of the drive element being radially displaced relative to the axis of the housing to produce a radial force of known magnitude and direction;
a fluid bearing means defined between the rotor and the housing; and
means for continually renewing the fluid in contact with all wetted surfaces on the chamber.

19. The pump as defined in claim 18 further comprising first and second radially spaced continuous flow passages defined between the rotor and the housing.

20. The pump as defined in claim 19 further comprising an opening through the rotor connecting the first and second passages for permitting flow therebetween.

21. The blood pump as defined in claim 19 wherein the rotor includes first and second sets of blades, the first blade set disposed in the first passage to pump fluid from the inlet to the outlet.

22. The pump as defined in claim 21 wherein the second blade set scavenges fluid from the second passage to enhance fluid through flow.

23. The blood pump as defined in claim 19 wherein the second passage is narrowed at one end to define a fluid bearing.

24. The pump as defined in claim 23 further comprising a groove in a side wall of the second passage to increase the area for flow through the fluid bearing.

25. The pump as defined in claim 23 wherein the second passage is narrowed at the other end to define a second fluid bearing.

26. The pump as defined in claim 25 further comprising a groove in a side wall of the second passage to increase the area for flow through the fluid bearing.

27. The pump as defined in claim 18 wherein the drive means includes an electric motor stator and winding in the housing portion and a surrounding permanent magnet assembly in the rotor.

28. The pump as defined in claim 18 wherein the magnetic attraction of the drive and driven elements of the rotating means define a thrust reaction means to resist longitudinal displacements caused by axial fluid, gravitational inertial or other forces.

29. The pump as defined in claim 18 further comprising means for limiting axial travel of the rotor relative to the housing.

30. The pump as defined in claim 29 wherein the limiting means includes a contact surface adapted to selectively contact the rotor.

31. The pump as defined in claim 18 wherein the housing includes a rotor housing a a motor housing each having its own axis, the axis of the rotor housing is radially displaced relative to the axes of the drive element of the drive means and the motor housing to provide closer alignment of a rotor housing axis with the rotor axis of rotation during operation.

32. The pump as defined in claim 18 wherein the drive means comprises a magnetic coupling in combination with a prime mover.

33. The pump as defined in claim 18 further comprising blood as the working fluid.

34. A rotodynamic blood pump comprising:
a housing having an inlet and an outlet in fluid communication with a chamber, the housing including a housing portion that extends axially inward to the chamber from an end wall;
an annular rotor receive in the chamber around the housing portion for selective rotation relative to the housing, the rotor being spaced from the housing and housing portion to define radially spaced first and second passages, the first passage extending between the inlet and outlet and containing an impeller blade set on the rotor for urging flow form the inlet to the outlet, and the second passage being narrowed at first and second ends to form fluid bearings;
drive means for rotating the rotor relative to the housing including a ferromagnetic assembly received in the rotor and an electric motor stator and winding assembly installed in the housing and radially coupled to the ferromagnetic assembly in the rotor, an axis of the motor stator being radially displaced relative to an axis of the housing to produce a radial force of known magnitude and direction; and
means for continually renewing the blood in contact with all wetted surfaces of the chamber.

35. The blood pump as defined in claim 34 wherein the magnetic attraction of the motor stator and ferromagnetic assembly defines a thrust reaction means to resist longitudinal displacements caused by axial fluid, gravitational, inertial or other forces.

36. The blood pump as defined in claim 34 wherein one end of the annular rotor is conically narrowed and cooperates with strut means on the rotor housing for limiting axial travel of the rotor relative to the housing.

37. The blood pump as defined in claim 34 further comprising means for urging blood flow through the second passage independent of the flow in the first passage.

38. The blood pump as defined in claim 34 further comprising a second blade set on the rotor for urging flow through the second passage.

39. The blood pump as defined in claim 34 further comprising an opening in the annular rotor connecting the first and second passages for permitting blood flow therebetween.

40. The blood pump as defined in claim 34 further comprising plural spaced grooves on the housing portion adjacent first and second ends of the second passage for increasing flow area through the fluid bearings.

41. The pump as defined in claim 40 wherein the the axis of the housing is radially displaced relative to the axes of the motor stator and the housing portion to provide closer alignment of the housing axis with the rotor axis of rotation during pumping.

* * * * *

(12) REEXAMINATION CERTIFICATE (4678th)

United States Patent
Golding et al.

(10) Number: US 5,324,177 C1
(45) Certificate Issued: Dec. 10, 2002

(54) SEALLESS ROTODYNAMIC PUMP WITH RADIALLY OFFSET ROTOR

(75) Inventors: Leonard A. R. Golding, Moreland Hills, OH (US); William A. Smith, Lyndhurst, OH (US)

(73) Assignee: The Cleveland Clinic Foundation, Cleveland, OH (US)

Reexamination Request:
No. 90/006,243, Mar. 8, 2002

Reexamination Certificate for:
Patent No.: 5,324,177
Issued: Jun. 28, 1994
Appl. No.: 07/695,312
Filed: May 3, 1991 07/695,312

Related U.S. Application Data

(63) Continuation-in-part of application No. 07/349,000, filed on May 8, 1989, now Pat. No. 5,049,134.

(51) Int. Cl.[7] .................................. F04B 17/00
(52) U.S. Cl. ................... 417/423.1; 417/423.7; 604/151; 415/900
(58) Field of Search .................... 417/423.1, 423.7, 417/354; 604/151; 415/900

(56) References Cited

U.S. PATENT DOCUMENTS

| | | |
|---|---|---|
| 3,218,981 A | 11/1965 | Kierulf |
| 3,846,050 A | 11/1974 | Laing |
| 4,135,253 A | 1/1979 | Reich et al. |
| 4,275,339 A | 6/1981 | Burke et al. |
| 4,382,199 A | 5/1983 | Isaacson |
| 4,438,542 A | 3/1984 | Schuh |
| 4,526,518 A | 7/1985 | Wiernicki |
| 4,688,998 A | 8/1987 | Olsen et al. |
| 4,779,614 A | 10/1988 | Moise |
| 4,806,080 A | 2/1989 | Mizobuchi et al. |
| 4,927,407 A | 5/1990 | Dorman |
| 4,944,748 A | 7/1990 | Bramm et al. |
| 4,957,504 A | 9/1990 | Chardack |
| 5,030,018 A | 7/1991 | Korenblit |
| 5,036,235 A | 7/1991 | Kleckner |
| 5,044,897 A | 9/1991 | Dorman |

*Primary Examiner*—Charles G Freay

(57) ABSTRACT

A sealless centrifugal blood pump is provided in which a rotatable impeller is supported in a pump housing by fluid bearings during operation. Rotational movement of the impeller is accomplished with an inverted motor for magnetically driving of the impeller and maintenance of the axial running position of the impeller relative to the housing. In an alternative embodiment, the axis of the rotor housing is radially displaced relative to the axes of drive element of the motor and the motor housing.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–41 is confirmed.

* * * * *